United States Patent [19]

Abramson

[11] 4,030,978
[45] June 21, 1977

[54] NOVEL ASSEMBLY, COMPOSITIONS AND METHODS
[75] Inventor: Irwin J. Abramson, Baltimore, Md.
[73] Assignee: Becton, Dickinson and Company, East Rutherford, N.J.
[22] Filed: July 29, 1976
[21] Appl. No.: 709,661
[52] U.S. Cl. .................................. 195/75; 195/99; 195/103.5 M; 195/127
[51] Int. Cl.² .......................................... C12K 1/04
[58] Field of Search ............ 195/103.5 M, 127, 99, 195/100, 102, 72, 74, 75

[56] References Cited
UNITED STATES PATENTS
3,715,281  2/1973  Martin, Jr. ........................ 195/100

OTHER PUBLICATIONS
Manual of Clinical Microbiology, 2nd, Ed., (1974), American Society for Microbiology, pp. 365-375 and 890.

Primary Examiner—Alvin E. Tanenholtz
Attorney, Agent, or Firm—Kane, Dalsimer Kane, Sullivan and Kurucz

[57] ABSTRACT

The disclosure is of a novel assembly and method for transporting aerobic, anaerobic and facultative microorganisms from clinical patient to laboratory. The disclosure is also of a novel protective medium for maintaining viability of microorganisms during transportation.

12 Claims, 8 Drawing Figures

NOVEL ASSEMBLY, COMPOSITIONS AND METHODS

BACKGROUND OF THE INVENTION

1. Field of the Invention

The invention concerns apparatus, methods and compositions for preserving the viability of microorganisms and more particularly concerns an assembly and composition for the protection of anaerobes from exposure to gaseous oxygen during the period of time between isolation from a clinical source and inoculation into a system for culturing and/or identification of the anaerobe.

2. Brief Description of the Prior Art

In recent years there has been an increased awareness of the importance of diagnosing infections caused by anaerobic microorganisms. Apparatus and techniques for culturing and differentiating anaerobic microorganisms has been developed and refined to isolate and differentiate anaerobic microorganisms in an infection site; see for example the apparatus disclosed in U.S. Pat. No,. 3,246,959. However, the weak link in the overall procedure of collecting an anaerobic clinical specimen, carrying the specimen to the laboratory and culturing the anaerobe therein has been in the transportation step. If in transporting the clinical specimen from the patient to the laboratory, the specimen is exposed to gaseous oxygen, the oxygen sensitive anaerobes may die and the subsequent differentiation is inaccurate. Many strains of anaerobic microorganisms are sensitive to oxygen especially in low numbers and may not survive even brief exposures to gaseous oxygen.

A review of the prior art methods and apparatus for transporting anaerobic microorganisms between clinical source and laboratory may be found in the Scope Monograph on Anaerobic Infections published by The Upjohn Company, Kalamazoo, Michigan, (1972; Library of Congress Card No. 72-79754) on pages 54–55. In brief, the reviewed methods describe either rapidly placing a swab containing a specimen into a carbon dioxide filled container or into a transport medium, or aspirate a liquid specimen into a syringe and then injecting the specimen into an anaerobe bottle or vial. The Scope Monograph describes transporting specimens suspected of containing anaerobe microorganisms on cotton swabs protected from exposure to oxygen by immersion in prereduced, anaerobically sterilized Cary-Blair medium in either a tube or a vial with a mineral oil overlay. In addition to the Cary-Blair reduced transport medium there are other commercially available reduced transport media commonly referred to as thioglycolate mediums. These include Amies medium, Stuart's, and thioglycolate-135C media. However, heretofore the employment of reduced thioglycolate transport media for preserving the viability of anaerobic microorganisms during collection and transport has not been completely encouraging; see for example Yrios et al, Abstracts of the Annual Meeting of the ASM (1974). In general, one of the major problems faced in transporting anaerobic microorganisms resides in maintaining the anaerobes in a viable condition without growth of either the anaerobes or other microorganisms present in the specimen over an extended period of time. This is particularly important for the accurate identification of pathogens whose presence may be masked by the overgrowth of saprophytic microorganisms.

Anaerobic microorganism transporting devices have been described previously; see for example U.S. Pat. Nos. 3,483,089; 3,750,646; 3,773,035; and 3,913,564. In spite of the fairly advanced state of the art, a number of problems remain to deny the art a perfect means of transporting anaerobic microorganisms from a patient to a laboratory. To mention a few, a number of prior art assemblies are not readily shipped without special precautions. A number of assemblies make no provision for preventing desiccation of the transported anaerobes. Many of the transporting devices can be opened only once for access to the contained anaerobes and their usefulness is thereafter lost. The assembly and method of the invention are relatively simple in comparison to the prior art apparatus and methods. The assembly of the invention is constructed readily at low cost and requires a minimum amount of training for operation. In addition, the assembly of the invention may be handled, shipped, and transported without many of the special precautions required of the prior art assemblies. Further, the method of the invention has shown great reliability in operation and assures transportation of viable anaerobic microorganisms even for prolonged periods of time. The assembly of the invention permits one to obtain minimal exposure of a clinical specimen to oxygen. The assembly and method of the invention, in conjunction with the composition of the invention will maintain anaerobic microorganisms viable for several days, without desiccation and without promotion of growth of the anaerobic microorganism or other microorganisms contained in the clinical specimen to be transported. Nor will the number of organisms be diluted by the composition of the invention because of the firmness of the composition in contrast to prior art compositions which are fluid or semi-solid in nature. Access to the transported anaerobes within the assembly may be had a plurality of times without compromising the performance of the invention. The composition of the invention is particularly advantageous in that while maintaining viability of anaerobic and other organisms, growth of microorganisms contained in the specimen is not promoted by the medium. Other advantages of the invention will be described in greater detail hereinafter.

SUMMARY OF THE INVENTION

The invention comprises an assembly for maintaining aerobic, anaerobic and facultative microorganisms, which comprises; a tubular container having a first, hermetically sealed end and a second end hermetically sealed with a removable closure, said container with said closure defining a collection chamber; a composition partially filling said collection chamber, said composition comprising, in parts by weight;

| | | |
|---|---|---|
| 1,000 | parts | ion free water |
| 0.001–0.5 | " | oxygen indicator |
| 1.8–2.2 | " | sodium phosphate, tribasic |
| 0.9–1.1 | " | potassium phosphate, dibasic |
| 0.09–0.11 | " | calcium chloride |
| 0.09–0.11 | " | magnesium chloride hexahydrate |
| 7.5–8.5 | " | sodium chloride |
| 0.5–1.5 | " | sodium thioglycolate |
| 0.5–1.5 | " | cysteine hydrochloride |
| 5–20 | " | agar; | said composition having a firmness or gel strength of from about 170–350 grams/centimeter square and having a pH of 6.9–7.8; the remaining portion of said collection chamber being filled with an oxygen free gas which comprises nitrogen and hydrogen.

The invention also comprises the composition described above, which is a useful medium for maintaining the viability of anaerobic microorganisms without promoting their growth.

The invention also comprises the method of protecting collected anaerobic microorganisms by transportation in the assembly of the invention and a method of preparing the assembly of the invention.

The assembly of the invention is also useful for transport and maintenance of viability of aerobic and facultative microorganisms.

BRIEF DESCRIPTIONS OF THE DRAWINGS

DETAILED DESCRIPTION OF THE INVENTION

For a complete understanding of the invention, the following description should be read in conjunction with the accompanying drawings of FIGS. 1–8, inclusive.

Figure 1:
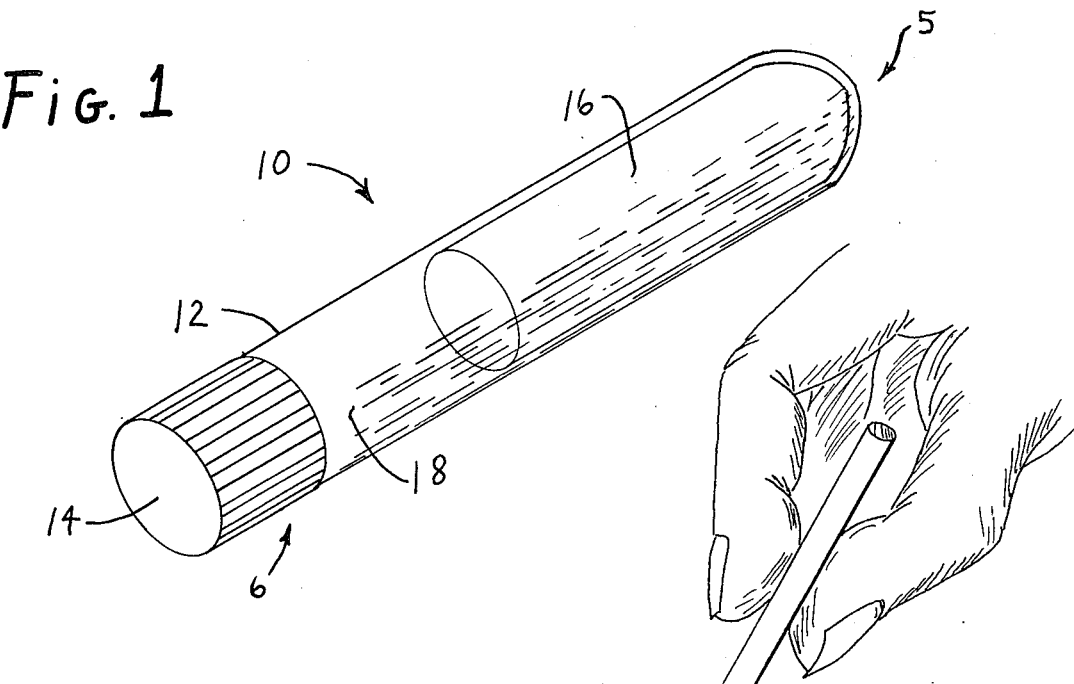
FIG. 1 is an isometric view of an embodiment assembly of the invention.

FIG. 1 is an isometric view of a preferred assembly 10 of the invention which consists of a tubular container 12 having hermetically sealed ends 5,6 and defining a hermetically sealed chamber 18. Container 12 may be fabricated from any material conventionally employed to construct laboratory apparatus, such as glass, gas impermeable polymerics and the like. Preferably, the material selected for fabrication of container 12 is transparent. End 5 of container 12 is an integral, closed end of the tubular container 12. End 6 is open and hermetically sealed with a removable cap closure 14. Preferably cap 14 is of the screw type with a gas sealing lining such as rubber or Teflon. Disposed in container 12 and partially filling the sealed chamber 18 is a colorless composition 16. The residue of chamber 18 is filled with an oxygen free gas, preferably 95% nitrogen and 5% hydrogen. Although the dimensions of assembly 10 and the depth of composition 16 are not critical to the invention, there are preferred dimensions. Preferably, the container 12 is a 16 × 125 millimeter flat bottom, No. 1 glass and the composition 16 fills approximately two-thirds of chamber 18. The greater the depth of composition 16, the greater will be protection of collected anaerobes from oxygen which may diffuse through composition 16.

The composition 16 disposed in the lower end of container 12 comprises, in parts by weight, 1,000 parts of ion free water (distilled or de-ionized water).

0.001–0.5 parts of an oxygen indicator such as resazurin or methylene blue. The preferred indicator is resazurin and the preferred proportion thereof is 0.001–0.003; most preferably 0.002.

1.8–2.2 (preferably 2.0) parts sodium phosphate tribasic.

0.9–1.1 (preferably 1.0) parts potassium phosphate, dibasic.

0.09–0.11 (preferably 0.1) parts calcium chloride.

0.09–0.11 (preferably 0.1) parts magnesium chloride hexahydrate.

7.5–8.5 (preferably 8.0) parts sodium chloride.

0.5–1.5 (preferably 1.0) parts sodium thioglycolate.

0.5–1.5 (preferably 1.0) parts cysteine hydrochloride.

5–20 (preferably 10) parts agar.

The composition 16 of the invention is basically a thioglycolate type of reducing medium prepared by first admixing all of the ingredients except the water. The resulting mixture is then added to the water in a suitable vessel. The aqueous mixture is then brought to reflux temperature to completely dissolve the solid ingredients and then cooled to circa 52° C. to 55° C. and maintained at this temperature until the mixture is of a color indicating the lack of oxygen presence. When the indicator compound is the preferred resazurin, the composition 16 will be colorless in the absence of oxygen. In the presence of oxygen, the color will range from a light pink to a blue to a lavender color. The pH of the final composition 16 as it will be found in the assembly 10 of the invention will be 6.9–7.8.

Basically, the composition 16 is a thioglycolate reducing medium comprising agar to inhibit diffusion of oxygen and to maintain an anaerobic microorganism specimen in a protected environment. An oxygen sensitive indicator such as resazurin is included to indicate the presence or absence of oxygen. Reducing agents to combine with and remove free oxygen include the sodium thioglycolate and the cysteine hydrochloride. The composition 16 will also evolve hydrogen sulfide gas over a period of time. This gas is of course an additional reducing agent which will combine with free oxygen introduced into the assembly 10. Salts are provided in composition 16 to maintain the anaerobes and phosphate buffers to maintain the pH of the medium. Each ingredient of the composition 16 is essential (with the exception of the oxygen indicator), in the proportions indicated, to maintain viability of anaerobe specimens entrusted to the protection of the assembly 10 of the invention. A particularly essential component of the composition 16 is from 1.8–2.2 parts by weight of the sodium phosphate, tribasic. The reason for this critical proportion of the sodium phosphate, tribasic is not fully understood. The composition 16, prepared as described above and allowed to cool to room temperatures will have a gel strength or consistency of from about 170 to about 350 grams per centimeter square, preferably 180 to 190 grams per centimeter square (ASTM Method D-217). This is important to the invention since it allows for encapsulation of the anaerobe specimen under all normal conditions of transportation as will be discussed in greater detail hereinafter.

The assembly 10 and its contents may be sterilized in a conventional autoclave. Sterilization has been found to be effected by heating at 120° C. for about 15 to 20 minutes under a pressure of about 15 psig. When hermetically sealed and sterilized, the assembly 10 has demonstrated a shelf life of at least 1 year when stored at room temperatures (circa 20 to 25° C.).

Figure 2:
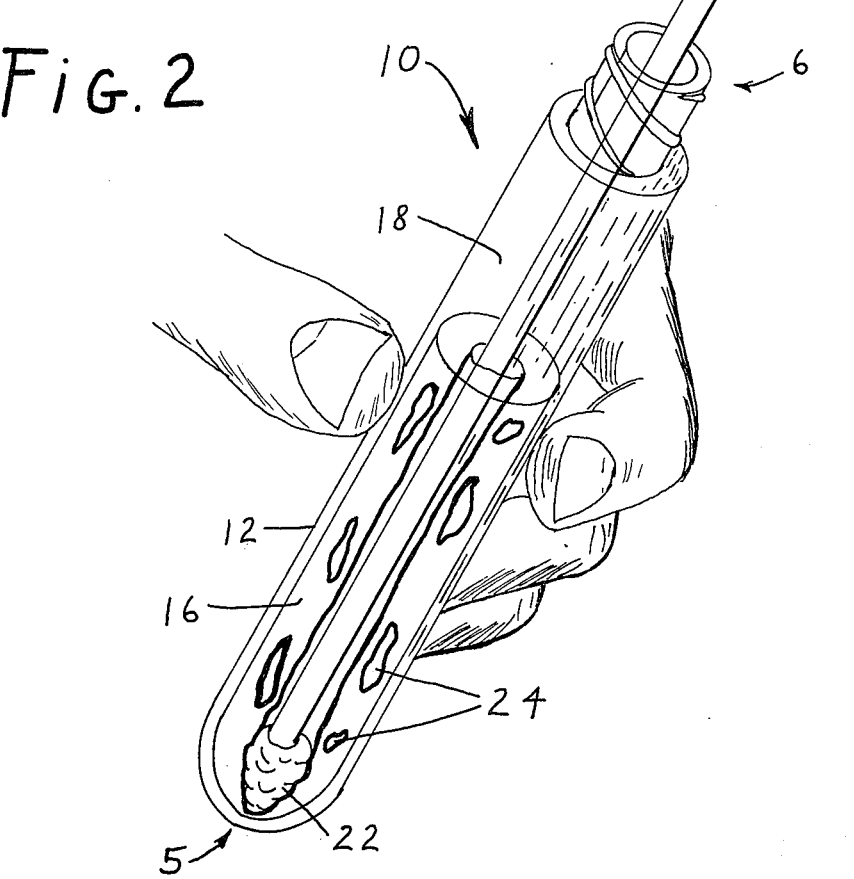
FIG. 2 is a view in perspective of the embodiment of FIG. 1 shown in initial use.

The method of the invention, employing assembly 10, is carried out by first removing screw cap 14 as shown in FIG. 2. While holding the assembly 10 in an upright position, a clinical specimen of transudate or exudate suspected of harboring anaerobic microorganisms, carried on the swab 22 of a swab stick 20 is inserted into the open end 6 of container 12 and positioned at the bottom of the column of composition 16 as shown in FIG. 2. In its passage through the column of composition 16, the swab 22 and stick 20 form a channel in the composition 16. Air carried into the chamber 18 is entrapped on the exposed surfaces of composition 16 and in air inclusions 24. Air of course will also be carried into the upper, composition free portion of chamber 18. After insertion of the swab 22, the stick 20 may be broken off at end 6 so that screw cap 14 may be replaced to hermetically reseal end 6 of container 12. Almost immediately, the areas of composition 16 exposed to air will indicate the presence of oxygen by a color change. When the preferred indicator is resazurin, a light pink to purple shade will be observed in the areas of composition 16 exposed to oxygen. Within a few moments, these areas of exposures generally expand as oxygen diffuses through specific zones or areas of the composition 16. This is illustrated in FIG. 3, a representation of the assembly 10 several minutes after insertion of swab 22.

Figure 3:
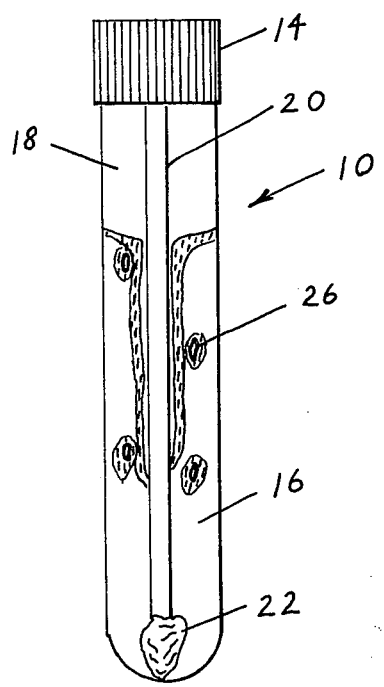
FIG. 3 is an isometric view of the embodiment of FIG. 1 shown holding a clinical specimen shortly after introduction thereof.
Figure 4:
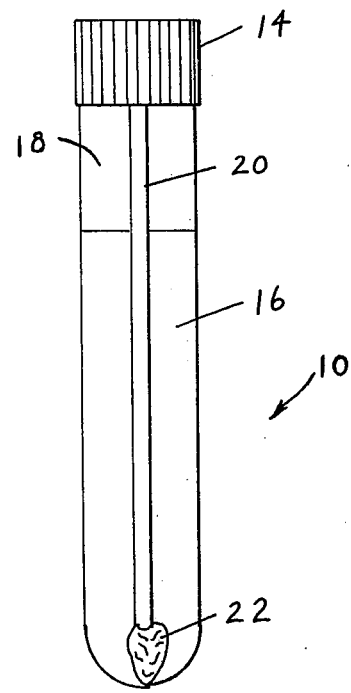
FIG. 4 is a view as in FIG. 3 but after reduction of oxygen introduced with the clinical specimen.

As seen in FIG. 3, within a few minutes after insertion of swab 22 and recapping of the assembly, the composition 16 begins to fill the channel caused by passage of swab 22. This occurs naturally from the selection of the consistency of composition 16 as described previously. Thus, the composition 16 encapsulates swab 22 and the microorganisms deposited thereon. The purple zones 26 shown in FIG. 3 indicate the presence of atmospheric oxygen. It will be noted in FIG. 3 that the lower portion of composition 16 is now free of oxygen, the reducing medium having reacted therewith. After one or two hours, the composition 16 will completely encapsulate the swab 22 and stick 20 as shown in FIG. 4. At this point in time, as also shown in FIG. 4, the colored zones have disappeared indicating the absence of oxygen which has been reduced by the reducing agents in composition 16. Generally, this will occur within several hours.

With the anaerobic microorganisms protected within composition 16 on swab 22, the assembly 10 as shown in FIG. 4 may be roughly handled, transported, etc., without removing the protective layer over swab 22. The consistency of composition 16 assures that there will be a protective layer over swab 22 as long as the agar remains intact. The firmness of composition 16 is also important to assure that there is no dilution of the collected microorganisms as would occur if composition 16 had a lower consistency, i.e.; a liquid rather than a firm gel-like material. This is important for maintaining lower bacterial counts.

Upon receipt of the assembly 10 in a laboratory, the cap 14 may be removed to gain access to chamber 18 of container 12. The technician may grasp stick with a sterile forceps and withdraw swab 22 for access to the microorganisms deposited thereon. The swab 22 may then be reinserted to the bottom of composition 16 and assembly 10 resealed. Access may be gained a plurality of times to swab 22 for the purpose of removing microorganisms for culture purposes. The composition 16 will repeatedly enclose, encapsulate and protect swab 22 while the reducing medium removes atmospheric oxygen which may accompany repeated openings of the assembly 10.

It should be noted that the composition 16 does not contain ingredients which would promote growth of microorganisms. This is important so that the specimen is maintained as collected without masking of anaerobic microorganisms by overgrowth of associated microorganisms. In a sense, the composition 16 may be described as a jejune environment which will sustain but not promote life of the microorganisms. There are no nutrients in the composition 16.

Figure 5:
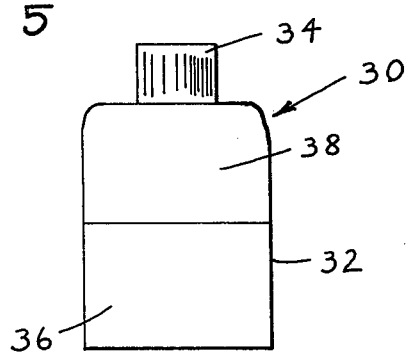
FIG. 5 is an isometric view of another embodiment assembly of the invention.

FIG. 5 is an isometric view of another embodiment assembly 30 of the invention and comprises a vial 32 including a cannulapenetrable closure 34. Following sealing of the assembly 30, the entire assembly may be sterilized using the same techniques and equipment described above in relation to assembly 10.

As previously described, it is important that the pH of the composition 16 or 36 be approximately 6.9–7.8 at the conclusion of sterilization.

Figure 6:
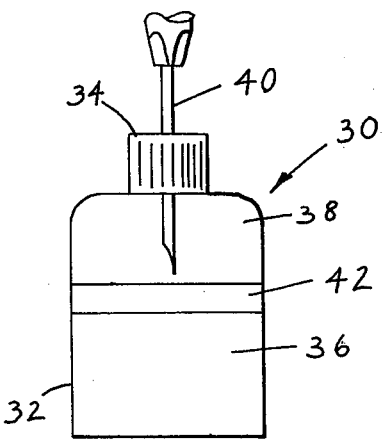
FIG. 6 is another view of the embodiment assembly of FIG. 5, upon initial use.
Figure 7:
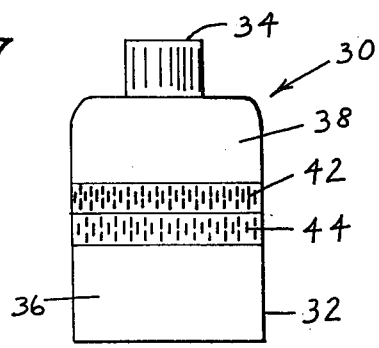
FIG. 7 is a view of the embodiment assembly of FIG. 6, shortly after the introduction of a clinical specimen with oxygen.
Figure 8:
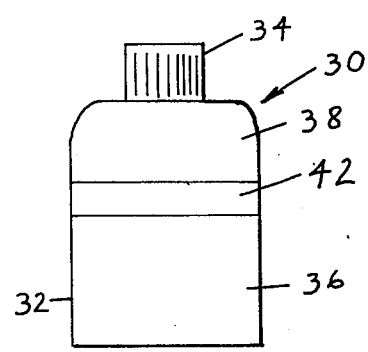
FIG. 8 is a view as seen in FIG. 7 but after the reduction of oxygen introduced with the clinical specimen.

Referring now to FIG. 6, the operation of assembly 30 will be described. The assembly 30 is used by first ejecting into the space 38 via a cannula 40 a liquid specimen suspected of harboring anaerobic microorganisms. On initial injection, the liquid specimen 42 will not appear to mix with composition 36. However, within minutes some of the ingredients of composition 36 apparently leach into specimen 42. Concurrently, any oxygen carried into chamber 38 with specimen 42 will begin to diffuse into composition 36. As shown in FIG. 7, a color change indicating the presence of oxygen will be noted in both specimen 42 and the upper zone 44 of composition 36. However, within a few hours the reducing ingredients of composition 36 will reduce the free oxygen and return the composition 36 and specimen 42 to their colorless condition as shown in FIG. 8. The specimen 42 will be maintained such that any anaerobic microorganisms contained therein will remain viable for several days. When desired, access to the specimen 42 may be obtained by piercing the closure 34 with a cannula and withdrawing any desired amount of the specimen 42. Again, any oxygen which is introduced when access to specimen 42 is obtained will be reduced by the reducing agent ingredients and the hydrogen sulfide generated by composition 36.

The following preparations and examples describe the manner and process of testing the efficacy of the invention and set forth the best mode contemplated by the inventor of testing the invention but are not to be construed as limiting.

| Preparation 1 Amies Preparation Ingredient | Weight or Volume |
|---|---|
| Agar | 3.6 grams |
| Sodium Thioglycolate | 1.0 grams |
| Di-sodium phosphate | 1.15 grams |
| Mono-potassium phosphate | 0.2 grams |
| Magnesium chloride | 0.1 grams |
| Calcium chloride | 0.1 grams |
| Potassium chloride | 0.2 grams |
| Sodium chloride | 8.0 grams |
| Distilled water | 1,000 milliliters |

The pH measured for the above preparation is 7.1.

| Preparation 2 | |
|---|---|
| A composition of the invention. | |
| Ingredient | Weight or Volume |
| Resazurin | 0.002 grams |
| Sodium phosphate, tribasic | 2.0 grams |
| Potassium phosphate, dibasic | 1.0 grams |
| Calcium chloride | 0.1 grams |
| Magnesium chloride hexahydrate | 0.1 grams |
| Sodium chloride | 8.0 grams |
| Sodium thioglycolate | 1.0 grams |
| Cysteine hydrochloride | 1.0 grams |
| Agar | 10.0 grams |
| Purified Water | 1,000 milliliters |

The pH of the above composition of Preparation 2 is adjusted to circa 7.2. After sterilization as hereinafter described, the pH is found to be 6.9–7.2.

A plurality of 16 × 125 milliliter flat bottom No. 1 glass tubes are arranged in three series. The first series is labelled A and receives 11 milliliters of the Preparation 1 supra. The second series is labelled B and receives 11 milliliters of the Preparation 2 supra. The third series is labelled C and serves as a control series. After dispensing Preparation 1 or 2 to series A and B, all tubes are purged of air by flushing with an oxygen free mixture of 95% nitrogen and 5% hydrogen. After flushing, all of the tubes are hermetically sealed with a screw top cap and sterilized in an autoclave at a temperature of 121° C. for 10–20 minutes under a pressure of about 15 psig. After sterilization, a representative tube from each of groups A and B is opened and the pH of the contained composition observed. It is found that the Preparation 1 in series A has a pH of about 7.1 whereas the pH of Preparation 2 contained in series B is about 6.9–7.2.

Swabs mounted on swab sticks are briefly immersed in dilute cultures of *Bacteroides melaninogenicus* (A762) assayed to have a viable count of $6.2 \times 10^6$ organisms/ml. and then inserted into each tube of the series A, B and C. The swabs are located or positioned at the bottom of the media composition contained in series A and B tubes. The tubes are resealed and maintained at a temperature of circa 25° C. for 72 hours. At the end of this period, the swabs are removed and streaked on Schaedler agar container 5% sheep blood and 10 μg of vitamin Kl/ml., incubated anaerobically for 72 hours and the colonies counted. The counts of microorganisms recovered from series A is $1 \times 10^4$ organisms/ml. The count of microorganisms recovered from series B tubes is $1.1 \times 10^7$ organisms/ml. No organisms were recovered from series C (control) tubes.

From the above experiment it is concluded that the viability of the microorganism was protected to a much higher degree in the series B assembly than in the Series A assembly or the control.

What is claimed:

1. An assembly for maintaining anaerobic, aerobic or facultative microorganisms, which comprises;
    a tubular container having a first, hermetically sealed end and a second end hermetically sealed with a removable closure, said container with said closure defining a collection chamber;
    a composition partially filling said collection chamber, said composition comprising, in parts by weight,
    1,000 parts ion free water
    0.01–0.5 parts oxygen indicator
    1.8–2.2 parts sodium phosphate, tribasic
    0.9–1.1 parts potassium phosphate, dibasic
    0.09–0.11 parts calcium chloride
    0.09–0.11 parts magnesium chloride hexahydrate
    7.5–8.5 parts sodium chloride
    0.5–1.5 parts sodium thioglycolate
    0.5–1.5 parts cysteine hydrochloride
    5–20 parts agar;
    said composition having a consistency of from about 170–350 grams/cm² and having a pH of 6.9–7.8;
    the remaining portion of said chamber being filled with an oxygen free gas.

2. The assembly of claim 1 wherein said consistency (gel strength) is from about 180 to 190 gms/cm².

3. The assembly of claim 1 wherein said gas consists of 95% nitrogen and 5% hydrogen.

4. The assembly of claim 1 wherein said oxygen indicator is resazurin.

5. The assembly of claim 1 wherein said composition consists essentially of
    1,000 parts ion free water
    0.002 parts resazurin
    2.0 parts sodium phosphate tribasic
    1.0 parts potassium phosphate dibasic
    0.1 parts calcium chloride
    0.1 parts magnesium chloride hexahydrate
    8.0 parts sodium chloride
    1.0 parts sodium thioglycolate
    1.0 parts cysteine hydrochloride
    10.0 parts agar.

6. A composition, which comprises; in parts by weight,
    1,000 parts ion free water
    0.01–0.5 parts oxygen indicator
    1.8–2.2 parts sodium phosphate, tribasic
    0.9–1.1 parts potassium phosphate, dibasic
    0.09–0.11 parts calcium chloride
    0.09–0.11 parts magnesium chloride hexahydrate
    7.5–8.5 parts sodium chloride
    0.5–1.5 parts sodium thioglycolate
    0.5–1.5 parts cysteine hydrochloride
    5–20 parts agar.

7. A composition according to claim 6 wherein said oxygen indicator is resazurin.

8. A composition according to claim 6, which comprises; in parts by weight,
    1,000 parts ion free water
    0.002 parts resazurin
    2.0 parts sodium phosphate tribasic
    1.0 parts potassium phosphate dibasic
    0.1 parts calcium chloride
    0.1 parts magnesium chloride hexahydrate
    8.0 parts sodium chloride
    1.0 parts sodium thioglycolate
    1.0 parts cysteine hydrochloride
    10.0 parts agar.

9. A method of maintaining viability of collected anaerobic, aerobic or facultative microorganisms, which comprises;
    providing an assembly, which comprises;
    a tubular container having a first, hermetically sealed end and a second end hermetically sealed with a removable closure, said container with said closure defining a collection chamber;
    a composition partially filling said collection chamber, said composition comprising, in parts by weight, 1,000 parts ion free water
0.01–0.5 parts oxygen indictor
1.8–2.2 parts sodium phosphate, tribasic
0.9–1.1 parts potassium phosphate, dibasic
0.09–0.11 parts calcium chloride
0.09–0.11 parts magnesium chloride hexahydrate.
7.5–8.5 parts sodium chloride
0.5–1.5 parts sodium thioglycolate
0.5–1.5 parts cysteine hydrochloride
5–20 parts agar;
said composition having a consistency (gel strength) of from about 170–350 gms/cm$^2$ and having a pH of 6.9–7.8; the unfilled portion of said chamber being filled with an oxygen free gas;
depositing a clinical specimen suspected of harboring pathogenic organisms into said chamber; and
hermetically sealing the open end of said container.

10. A method according to claim 9 wherein said composition comprises;
1,000 parts ion free water
0.002 parts resazurin
2.0 parts sodium phosphate tribasic
1.0 parts potassium phosphate dibasic
0.1 parts calcium chloride
0.1 parts magnesium chloride hexahydrate
8.0 parts sodium chloride
1.0 parts sodium thioglycolate
1.0 parts cysteine hydrochloride
10.0 parts agar.

11. A method according to claim 9 wherein said depositing of the clinical specimen is underneath the upper surface of said composition.

12. A method according to claim 9 wherein said depositing is under the surface of said composition.

* * * * *